United States Patent
Takase et al.

[11] Patent Number: 5,707,998
[45] Date of Patent: Jan. 13, 1998

[54] NITROGEN-CONTAINING FUSED-HETEROCYCLE COMPOUNDS

[75] Inventors: Yasutaka Takase; Nobuhisa Watanabe; Hideyuki Adachi; Kohtaro Kodama; Hiroki Ishihara; Takao Saeki; Shigeru Souda, all of Ibaraki, Japan

[73] Assignee: Eisai Co., Ltd., Japan

[21] Appl. No.: 525,739

[22] PCT Filed: Mar. 18, 1994

[86] PCT No.: PCT/JP94/00446

§ 371 Date: Sep. 25, 1995

§ 102(e) Date: Sep. 25, 1995

[87] PCT Pub. No.: WO94/22855

PCT Pub. Date: Oct. 13, 1994

[30] Foreign Application Priority Data

Mar. 31, 1993 [JP] Japan ................. 5-095131

[51] Int. Cl.$^6$ .................. C07D 403/00; C07D 403/02; C07D 239/94; A61K 31/505
[52] U.S. Cl. ................. 514/259; 514/260; 544/291; 544/293
[58] Field of Search ................. 544/283, 291, 544/293; 514/259, 260

[56] References Cited

U.S. PATENT DOCUMENTS

| | | | |
|---|---|---|---|
| 5,350,749 | 9/1994 | Hackler et al. | 514/248 |
| 5,436,233 | 7/1995 | Lee et al. | 514/63 |
| 5,439,895 | 8/1995 | Lee et al. | 514/63 |
| 5,457,105 | 10/1995 | Barker | 514/234.5 |
| 5,475,001 | 12/1995 | Barker | 514/258 |
| 5,576,322 | 11/1996 | Takase et al. | 514/260 |

FOREIGN PATENT DOCUMENTS

| | | |
|---|---|---|
| 209089 | 7/1987 | European Pat. Off. . |
| 385850 | 9/1990 | European Pat. Off. . |
| 414386 | 2/1991 | European Pat. Off. . |
| 510235 | 10/1992 | European Pat. Off. . |
| 9207847 | 5/1992 | WIPO . |
| 9307142 | 4/1993 | WIPO . |

OTHER PUBLICATIONS

Gazengel et al., J. Het. Chem. 26 (1989) 1135–1139.
Hayes et al., Tetrahedron 48(6), 2089–2096, (1990).
Brown et al., J. C. S. Perkins Transactions, 1(21), 2182–5, 1975.
Soloducho, Archio Der Pharmazie, 323(8), 513–5, 1990.
Godefroy et al., J. Het. Chem., 10(6), 1077–8, 1973.

*Primary Examiner*—Matthew V. Grumbling
*Attorney, Agent, or Firm*—Nixon & Vanderhye

[57] ABSTRACT

The present invention relates to a nitrogen-containing heterocyclic compound exhibiting an inhibitory activity against cGMP-PDE. The compound represented by the formula (I) or a pharmacologically acceptable salt thereof:

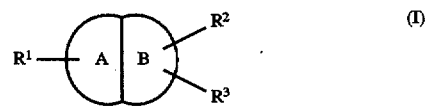

wherein $R^1$ represents a group represented by the formula: —$NR^4R^5$ (wherein $R^4$ and $R^5$ each represent hydrogen, lower alkyl or the like) or the like; $R^2$ represents a group represented by the formula:

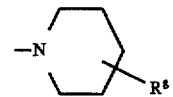

(wherein $R^8$ represents a carboxyl group which may be protected, or the like) or the like; and $R^3$ represents a group represented by the formula:

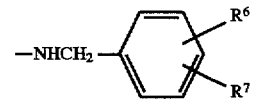

(wherein $R^6$ and $R^7$ each represent hydrogen, lower alkyl or the like) or the like.

4 Claims, No Drawings

NITROGEN-CONTAINING FUSED-HETEROCYCLE COMPOUNDS

This a national stage application filed under 35 U.S.C. §371 of PCT/JP94/00446, filed Mar. 18,1994.

FIELD OF INDUSTRIAL APPLICATION

The present invention relates to a nitrogenous fused-heterocycle compound which exhibits an excellent activity as a drug.

BACKGROUND OF THE INVENTION AND PRIOR ART

Angina pectoris which is one of ischemic heart diseases has been known as a disease which often attacks the aged. Nitrates, nitrites, calcium antagonists and β-blockers have been used as a remedy therefor, but they are still poorly effective in treating angina pectoris and in preventing the evolution thereof to myocardial infarction. Further, there have recently been observed lowering in the age of a patient with angina pectoris and complication in the symptoms thereof which are caused by stress enhanced by changes in the life style and complication in the social system and so on. Under these circumstances, the development of a new type of excellent drug has been expected.

It is believed in respect of the nitrate and nitrite compounds among the above current angina pectoris remedies that cyclic GMP (hereinafter abbreviated to "cGMP")among the cyclic nucleotides known as the intracellular second messenger participates in the action of these compounds. Further, cGMP is well known to have a relaxant activity on the smooth muscle of the vessel or bronchus. Although the mechanism of action of the above remedy is not always apparent, it is generally believed that the relaxant activity of cGMP is due to the synthesis of cGMP accelerated by the activation of guanylate cyclase. However, the above remedies exhibit a low bioavailability and a relatively short reaction time. Further, it has been reported that they give rise to tolerance when administered repeatedly, which poses a clinical problem.

Under these circumstances, the inventors of the present invention have started studies to develop a new type of more excellent drug.

Namely, the inventors of the present invention directed their attention to cGMP phosphodiesterase (hereinafter abbreviated to "cGMP-PDE) inhibitory activity and have made intensive studies on compounds having such an activity for many years. As a result of the studies, the inventors of the present invention have found that a nitrogenous fused-heterocycle compound which will be described below has a cGMP-PDE inhibitory activity and is efficacious against various ischemic heat diseases. The present invention has been accomplished on the basis of this finding.

Quinazoline derivatives useful as drugs are disclosed in, e.g., Japanese Patent Application "Kohyo" (Published Japanese Translation of PCT Patent Application) No. 502462/1990, but they are different from the compounds of the present invention in structure and activity.

DISCLOSURE OF THE INVENTION

The present invention relates to a nitrogenous fused-heterocycle compound represented by the following general formula (I) and pharmacologically acceptable salts thereof:

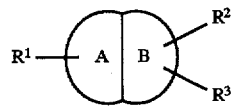

wherein ring A represents a benzene, pyridine or cyclohexane ring and ring B represents a pyridine, imidazole or pyrimidine ring, with the proviso that rings A and B are bonded to each other with two atoms being shared by them, and the shared atoms may be any of carbon and nitrogen atoms;

$R^1$ represents a group represented by the formula: —$NR^4R^5$ (wherein $R^4$ and $R^5$ may be the same or different from each other and each represent a hydrogen atom, a lower alkyl or acyl group or a carboxyl group which may be protected, or alternatively $R^4$ and $R^5$ may form a ring together with the nitrogen atom to which they are bonded, provided that the ring may be substituted), or a heteroaryl group which has one or two nitrogen atoms and may be substituted;

$R^2$ represents a hydrogen atom, a group represented by the formula:

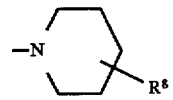

(wherein $R^8$ represents a carboxyl or tetrazolyl group which may be protected), or a halogen atom; and $R^3$ represents a hydrogen atom or a group represented by the formula:

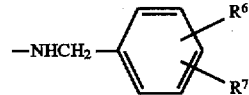

(wherein $R^6$ and $R^7$ each represent a hydrogen or halogen atom or a lower alkoxy group, or alternatively $R^6$ and $R^7$ may together form a methylenedioxy or ethylenedioxy group).

In the definition of the general formula (I), the lower alkyl group defined with respect to $R^4$ and $R^5$ is a linear or ranched alkyl group having 1 to 6 carbon atoms, and examples thereof include methyl, ethyl, n-propyl, n-butyl, isopropyl isobutyl, 1-methylpropyl, tert-butyl, n-pentyl, 1-ethylpropyl, isoamyl and n-hexyl groups, among which methyl and ethyl groups are the most desirable.

The lower alkoxy group defined with respect to $R^6$ and $R^7$ is one derived from the above lower alkyl group, and preferable examples thereof include methoxy and ethoxy groups.

As described above, $R^4$, $R^5$ and $R^8$ may each be a carboxyl group which may be protected and the protecting group applicable to this case includes lower alkyl groups, e.g., methyl, ethyl and t-butyl groups; phenyl-substituted lower alkyl groups wherein the phenyl group may be substituted, e.g., p-methoxybenzyl, p-nitrobenzyl, 3,4-dimethoxybenzyl, diphenylmethyl, trityl and phenethyl groups; halogenated lower alkyl groups, e.g., 2,2,2-trichloroethyl and 2-iodoethyl groups; lower alkanoyloxy lower alkyl groups, e.g., pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl groups; higher alkanoyloxy lower alkyl groups, e.g., palmitoyloxyethyl, heptadecanoyloxymethyl and 1-palmitoyloxyethyl groups; lower alkoxycarbonyloxy lower alkyl groups, e.g., methoxycarbonyloxymethyl, 1-butoxycarbonyloxyethyl and 1-(isopropoxycarbonyloxy) ethyl groups; carboxy lower alkyl groups, e.g., carboxymethyl and 2-carboxyethyl groups; heterocyclic groups, e.g., 3-phthalidyl group; benzoyloxy lower alkyl groups wherein the benzoyl group may be substituted, e.g., 4-glycyloxybenzoyloxymethyl and 4-[N-(t-butoxycarbonyl) glycyloxy]benzoyloxymethyl groups; (substituted dioxolene) lower alkyl groups, e.g., (5-methyl-2-oxo-1,3-dioxolen-4-yl)methyl group; cycloalkyl-substituted lower alkanoyloxy lower alkyl groups, e.g., 1-cyclohexylacetyloxyethyl group; and cycloalkyloxycarbonyloxy lower alkyl groups, e.g., 1-cyclohexyloxycarbonyloxyethyl group.

Further, the carboxyl group may be protected in the form of various acid amides. In other words, the protecting group may be any one so far as it can be decomposed into a free carboxyl group in vivo. The compound of the present invention exhibits an activity as a drug when deblocked in vivo or as such.

The acyl group defined with respect to $R^4$ and $R^5$ is an aliphatic or aromatic one or one derived from a heterocycle and examples thereof include lower alkanoyl groups such as formyl, acetyl, propionyl, butyryl, valeryl, isovaleryl and pivaloyl groups; aroyl groups such as benzoyl, toluoyl and naphthoyl groups; and heteroaroyl groups such as furoyl, nicotinoyl and isonicotinoyl groups, among which formyl, acetyl and benzoyl groups are preferable.

The "heteroaryl group which has 1 to 2 nitrogen atoms and may be substituted" as defined with respect to $R^1$ includes pyridyl, pyrrolyl, imidazolyl, pyrazolyl, pyrazyl, pyrimidyl and pyridazyl groups, though it is not limited to them.

The substituent for the above heteroaryl group includes hydroxyl and nitro groups; halogen atoms such as chlorine, fluorine, bromine and iodine atoms; lower alkyl groups such as methyl, ethyl and t-butyl groups; lower alkoxy groups such as methoxy, ethoxy and t-butoxy groups; carboxyl group which may be protected; and hydroxyalkyl, carboxyalkyl and tetrazolyl groups.

As described above, $R^4$ and $R^5$ may form a ring together with the nitrogen atom to which they are bonded, and the ring may be substituted. The substituent for the ring is the same as the one described above.

The halogen atom defined with respect to $R^6$ and $R^7$ includes fluorine, chlorine, bromine and iodine atoms.

In the general formula (I), the ring moiety is constituted of a fused ring composed of rings A and B. Preferable examples thereof are as follows:

a)
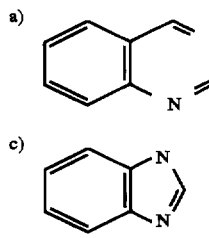

b)
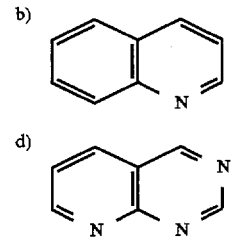

c)
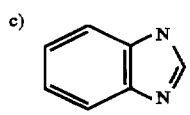

d)
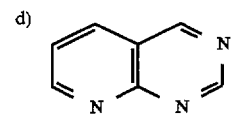

e)
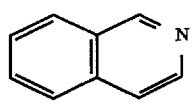

f)
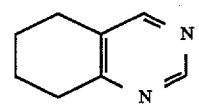

Among these fused rings, the rings (a), (b), (c), (d) and (e) are still preferable. The followings are more preferable:

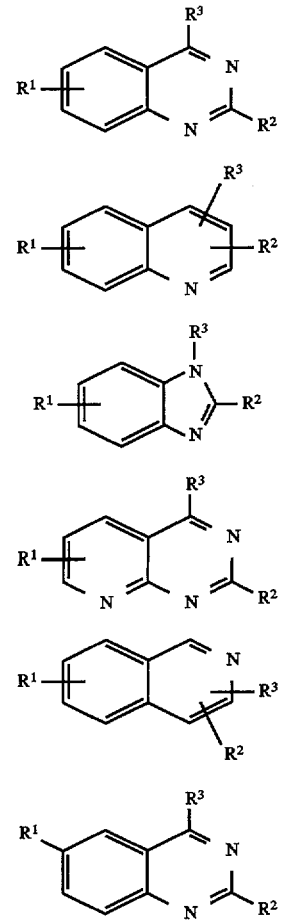

(III)

(IV)

(V)

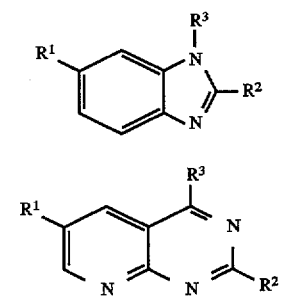

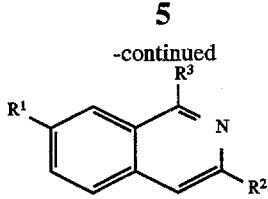

The pharmacologically acceptable salt according to the present invention includes inorganic acid salts such as hydrochloride, sulfate, hydrobromide and phosphate; and organic acid salts such as formate, acetate, trifluoroacetate, maleate, fumarate, tartrate, methanesulfonate, benzenesulfonate and toluenesulfonate.

Further, the compounds of the present invention may be present as hydrates and it is needless to say that the present invention includes these hydrates.

The compounds of the invention can be prepared by the following processes. They are described in respect to the compounds having the formula (I) in which B is a pyrimidine ring. The other compounds, such as pyridine and imidazol, can be prepared according to the below disclosed processes, using a corresponding starting material to (VII).

Preparation Process 1

A compound represented by the general formula (I-2) can be prepared by the following process:

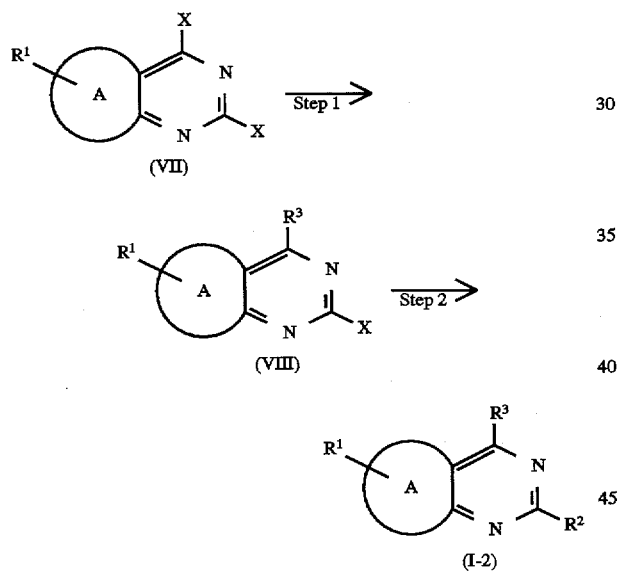

wherein $R^1$, $R^2$ and $R^3$ are each as defined above; and X and X' may be the same or different from each other and each represent a halogen atom.

(Step 1)

In this step, condensation is conducted in the conventional manner. The compound (VII) is subjected to condensation with $R^3$—H to obtain the compound (VIII)

The solvent to be used in this reaction may be any one inert to the teacron and preferable examples thereof include alcohols such as isopropyl alcohol, ethers such as tetrahydrofuran, and dimethylformamide.

More desirable results can be attained, when the condensation is conducted by heating under reflux in the presence of a tertiary amine such as triethylamine while removing formed hydrochloric acid.

(Step 2)

In this step, the compound (VIII) prepared in the step 1 is condensed with a compound represented by the general formula: $R^2$—H in the conventional manner to obtain the compound (I-2).

The solvent to be used in this reaction may be any one inert to the reaction and preferable examples thereof include alcohols such as isopropyl alcohol, ethers such as tetrahydrofuran, and dimethylformamide.

When $R^2$ is bonded to the ring moiety through a nitrogen atom, it is preferable that the above condensation be conducted by heating under reflux in the presence of an organic base such as triethylamine, pyridine or ethyldiisopropylamine, an inorganic base such as sodium carbonate, potassium carbonate, sodium hydrogencarbonate, sodium hydride or sodium hydroxide, or an alkoxide such as sodium methoxide or potassium t-butoxide.

Preparation Process 2

A compound represented by the general formula (II) wherein $R^3$ is hydrogen can also be prepared by the following process:

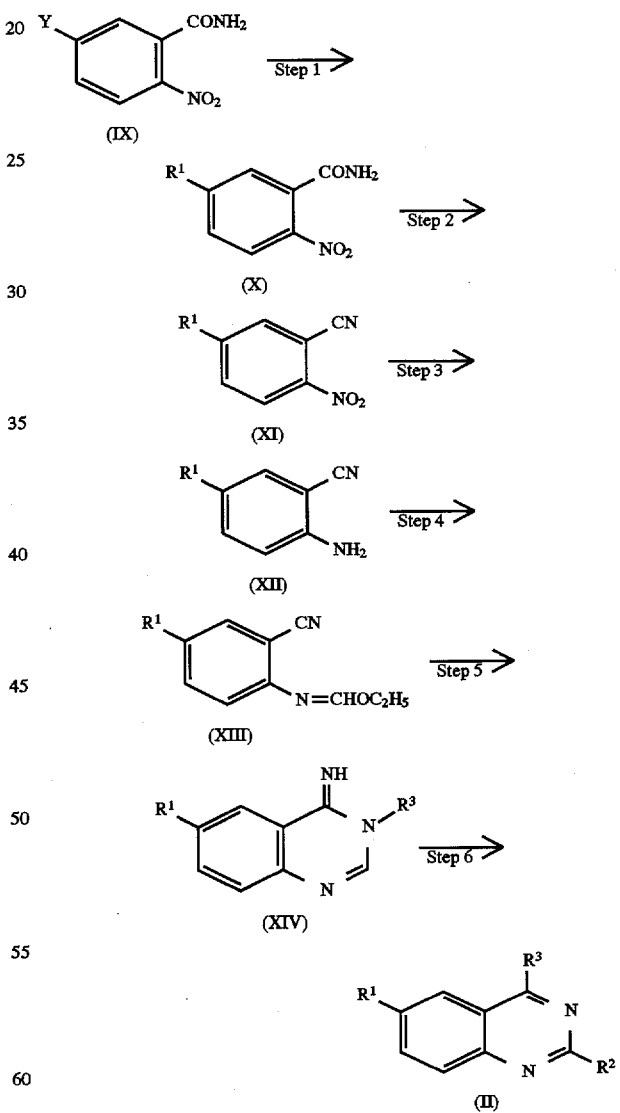

wherein $R^1$, $R^2$ and $R^3$ are each as defined above; and Y represents a halogen atom.

(Step 1)

In this step, a compound (X) is prepared by reacting a halogenated benzene derivative (IX) with an amine corresponding to a desired compound in a solvent in the presence of a base at a temperature ranging from room temperature to the boiling point of the solvent. The solvent is preferably tetrahydrofuran, N,N-dimethylformamide or N-methylpyrrolidone, though it may be any one inert to the reaction.

Preferable examples of the above base include potassium carbonate, hydrides of alkali and alkaline earth metals such as lithium hydride and calcium hydride, alkoxides such as potassium t-butoxide and sodium ethoxide, and sodium amide.

(Step 2)

In this step, the benzamide derivative prepared in the step 1 is dehydrated into a compound (XI).

This dehydration is generally conducted under heating, though it can proceed enough even at room temperature. Preferable examples of the dehydrating reagent usable in this case include trifluoroacetic anhydride, thionyl chloride, chlorosulfonyl isocyanate, p-toluenesulfonyl chloride, phosphorus pentachloride and phosphorus oxychloride.

The solvent to be uses in the reaction is preferably an ether such as tetrahydrofuran or dioxane, acetonitrile, N,N-dimethylformamide, triethylamine or pyridine, though it may be any one inert to the reaction.

(Step 3)

In this step, the nitrobenzene derivative prepared in the step 2 is reduced into an aniline derivative represented by the general formula (XII).

This reduction is preferably conducted in a polar solvent, for example, water or an alcohol such as methanol or ethanol.

The reduction is generally conducted under an acidic condition with acetic or hydrochloric acid in the presence of a metal such as iron, tin or zinc.

The reaction temperature may range from room temperature to the refluxing temperature of the solvent used.

(Step 4)

In this step, a compound represented by the general formula (XIII) is prepared by heating the aniline derivative prepared in the step 3 in ethyl orthoformate in the presence of an acid such as trifluoroacetic, p-toluenesulfonic or concentrated hydrochloric acid.

(Step 5)

In this step, the compound (XIII) prepared in the step 4 is condensed with an amine corresponding to a desired compound (XIV) in the conventional manner to conduct ring closure.

The solvent to be used in this condensation may be an alcohol such as methanol or ethanol. The reaction temperature is preferably about 50° C., though it may range from room temperature to the boiling point of the solvent used.

(Step 6)

In this step, an objective compound (II) is prepared by heating the compound (XIV) prepared in the step 5 in a solvent.

The solvent to be used in the reaction is preferably an alcohol such as methanol or ethanol, though it may be any one inert to the reaction.

More desirable results can be attained by conducting the reaction in the presence of an alkali such as aqueous sodium hydroxide or potassium carbonate.

Preparation Process A

The starting material (VII-2) used in the preparation of a compound represented by the general formula (I-2) wherein the ring moiety is quinazoline can be prepared by the following process:

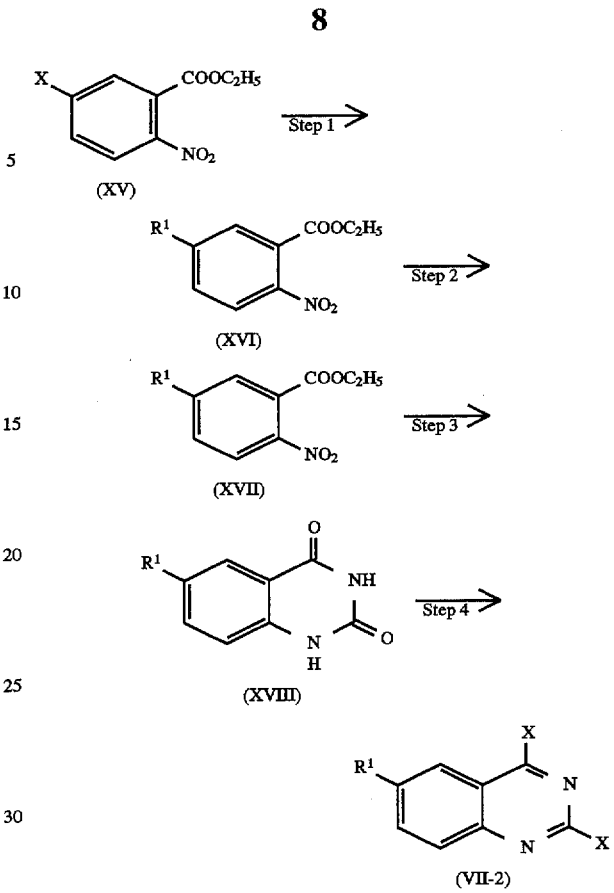

The invention provides a method for preventing or therapeutically treating diseases against a phosphodiesterase-inhibiting action is efficacious, which comprises administering a mammal subject with a pharmacologically effective amount of the compound as above defined (I) or a pharmacologically acceptable salt thereof.

It is preferable that the subject is human being; the diseases are those against which a cyclic GMP phosphodiesterase-inhibiting action is efficacious; the diseases are those selected from ischemic heart diseases, angina pectoris, hypertension, heart failure and asthma.

The invention provides use of the compound (I) or a pharmacologically acceptable salt thereof for manufacturing a preventive or therapeutic agent for diseases against a phosphodiesterase-inhibiting action is efficacious; and a preventive or therapeutic agent for diseases against a phosphodiesterase-inhibiting action is efficacious, comprising the compound (I) or a pharmacologically acceptable salt thereof.

The invention provides a process for producing the compound (I), in which B is pyrimidine ring, $R^2$ is attached to the 2-position and $R^3$ is attached to the 4-position, comprising the steps of (1) condensing a compound (VII) with a compound having the formula $R^3$—H to obtain a compound (VIII) and then (2) condensing the compound (VIII) with a compound having the formula $R^2$—H to obtain a compound (I-2); and a process for producing the compound (I), being a 6-$R^1$-2-$R^2$-4-$R^3$-quinazoline compound, $R^3$ is hydrogen atom, which comprising the steps of (1) reacting a compound (IX) with an amine compound to obtain a compound (X), (2) dehydrating the compound (X) to obtain a compound (XI), (3) reducing the compound (XI) to obtain an aniline compound (XII), (4) heating the compound (XII) with ethyl ortho-formate and an acid to obtain a compound (XIII), (5) reacting the compound (XIII) with an amine for cyclization and condensation to obtain a compound (XIV) and (6) heating the compound (XIV) to obtain the compound (II).

A pharmacological experimental example will now be described to illustrate the usefulness of the compounds of the present invention in detail.

PHARMACOLOGICAL EXPERIMENTAL EXAMPLE

Inhibitory Activity Against cGMP-PDE Prepared from Porcine Aorta

1. Experimental Method

The enzymatic activity of cGMP-PDE prepared from porcine aorta was determined by the method of Thompson et al. This determination was conducted in the presence of 1 mM EGTA by the use of 1 µM cGMP as the substrate. The compound of the present invention was added to the reaction system in a state dissolved in DMSO to determine its inhibitory activity. The final DMSO concentration of the reaction system was adjusted to 4% or below.

The above cGMP-PDE was prepared as follows:

Porcine aorta was cut into small pieces, followed by the addition of 10 times (by volume) as much buffer A [comprising Tris/HCl (20 mM), magnesium acetate (2 mM), dithiothreitol (1 mM), EDTA (5 mM), aprotinin (1400TIU/l), leupeptin (10 mg/l), benzamidine (1 mM) and PMSF (0.2 mM) and having a pH of 7.5]. The resulting mixture was homogenated and centrifuged at 100,000×g for one hour. The obtained supernatant was adsorbed on a column packed with DEAE-Toyopearl 650S (Tosoh, Tokyo, Japan). The resulting column was washed with buffer B [comprising Tris/HCl (50 mM), EGTA (0.1 mM), magnesium acetate (2 mM), dithiothreitol (1 mM) and PMSF (0.2 mM) and having a pH of 7.5] and thereafter subjected to gradient elution with 0.05 to 0.4M sodium chloride to give a CaM-independent cGMP-PDE fraction.

2. Experimental Results

The compounds of the present invention were examined for cGMP-PDE inhibitory activity by the above method and the results are given in Table 1.

TABLE 1

| Ex. No. | cGMP-PDE inhibitory activity ($IC_{50}$) |
|---|---|
| 2 | 120 nM |
| 7 | 148.3 |
| 10 | 18.7 |
| 4 | 1220 |
| 5 | 33.4 |
| 3 | 5.27 |
| 8 | 3.50 |
| 11 | 0.76 |
| 12 | 1130 |
| 1 | 9.9 |
| 6 | 8.09 |
| 9 | 1.48 |
| 15 | 360 |
| 14 | 720 |
| 17 | 403 |
| 13 | 7.29 |

It can be understood from the results of the Pharmacological Experimental Example that each of the compounds of the present invention has an inhibitory activity against PDE, particularly cGMP-PDE. In other words, it can be understood that the compound of the present invention has an effect of inhibiting cGMP-PDE to thereby enhance the in vivo cGMP level. Accordingly, the nitrogenous fused-heterocycle compound of the present invention is effective in the prevention and treatment of diseases against which a cGMP-PDE inhibitory activity is efficacious. Such diseases include ischemic heart diseases such as angina pectoris, myocardial infarction and chronic and acute heart failures; pulmonary hypertension which is complicated with cor pulmonale or not; hypertension resulting from any cause; peripheral circulatory failure; cerebral vascular insufficiency; cerebral dysfunction; and allergic diseases such as bronchial asthma, atopic dermatitis and allergic rhinitis.

Further, the compounds of the present invention are less toxic and highly safe, thus being valuable also in this sense.

When the compounds of the present invention are used as drugs, they may be each administered orally or parenterally. The dose thereof varies depending upon the extent of symptom, the age, sex, weight and drug sensitivity of a patient, the method, timing and interval of administration, the kind of pharmaceutical preparation, the kind of other drug administered together therewith, and the kind of the active ingredient, and is not particularly limited.

When the compound is administered orally, the dose thereof per adult a day is about 0.1 mg, which is administered in 1 to 3 portions a day.

When the compound is administered as an injection, the dose thereof a day is generally about 1 to 3000 µg/kg, preferably about 3 to 1000 µg/kg.

A solid preparation for oral administration according to the present invention is prepared by adding a filler and, if necessary, a binder, disintegrator, lubricant, color and/or corrigent to an active ingredient and shaping the obtained mixture into a tablet, coated tablet, granule, powder or capsule in the conventional manner.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc and polyethylene; those of the lubricant include magnesium stearate, talc, polyethylene glycol, silica and hardened vegetable oil; those of the color include those authorized as pharmaceutical additives; and those of the corrigent include cocoa powder, mentha herb, aromatic powder, mentha oil, borneol and powdered cinnamon bark. Of course, the tablet and granule may be suitably coated with sugar, gelatin or the like, if necessary.

An injection according to the present invention is prepared by adding a pH modifier, buffer, suspending agent, solubilizing agent, stabilizer, tonicity agent and/or preservative to an active ingredient at need and formulating the obtained mixture into an injection for intravenous, subcutaneous or intramuscular administration in the conventional manner. If necessary, the injection may be freeze-dried according to the conventional method.

Examples of the suspending agent include methylcellulose, Polysorbate 80, hydroxyethylcellulose, acacia, tragacanth powder, carboxymethylcellulose sodium and polyoxyethylene sorbitan monolaurate.

Examples of the solubilizing agent include polyoxyethylene hardened castor oil, Polysorbate 80, nicotinamide, polyoxyethylene sorbitan monolaurate, Macrogol and ethyl ester of castor oil fatty acids.

Examples will now be described to make the understanding of the present invention easier, being preceded by Preparative Examples in which the starting materials used in preparing the compounds of the present invention are prepared.

EXAMPLE

Preparative Example 1

Ethyl 2-nitro-5-(pyrazol-1-yl)benzoate

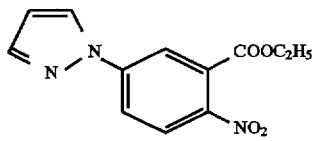

25.0 g (0.109 mol) of ethyl 5-chloro-2-nitrobenzoate and 9.00 g (0.132 mol) of pyrazole were dissolved in 120 ml of dimethylformamide. 4.60 g (0.115 mol) of sodium hydride was added in portions to the obtained solution under stirring at room temperature to conduct an exothermic reaction. The reaction mixture was cooled by allowing to stand and poured into water. The resulting mixture was extracted with ethyl acetate. The organic phase was washed with a saturated aqueous solution of common salt, dried over anhydrous magnesium sulfate and filtered. The filtrate was distilled in a vacuum to remove the solvent. The obtained residue was purified by silica gel column chromatography (with ethyl acetate/hexane) and recrystallization (from ethyl acetate/hexane) to give 17.2 g of a pale-yellow crystal.

Mol. formula (M.W.) $C_{12}H_{11}N_3O_4$ (261.24)

M.p. 85°–86° C.

MASS m/e; 262 ($M^+$+1)

Elemental anal. as $C_{12}H_{11}N_3O_4$ calcd. C=55.17 H=4.24 N=16.09 found. C=55.20 H=4.09 N=16.09

$^1$H-NMR δ (CDCl$_3$); 1.39(3H, t, J=7.2 Hz) 4.44(2H, q, J=7.2 Hz) 6.57(1H, dd, J=1.6, 2.8 Hz) 7.81(1H, d, J=1.6 Hz) 7.96(1H, dd, J=2.4, 8.8 Hz) 8.01(1H, d, J=2.4 Hz) 8.04(1H, d, J=2.8 Hz) 8.12(1H, d, J=8.8 Hz)

Preparative Example 2

Ethyl 2-amino-5-(pyrazol-1-yl)benzoate

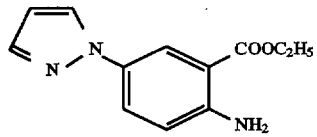

0.5 g of 10% palladium/carbon powder was added to 100 ml of an ethyl acetate solution of 10.0 g (38.3 mmol) of the ethyl 2-nitro-5-(pyrazol-1-yl)benzoate prepared in the Preparative Example 1. The resulting mixture was kept under pressuring with hydrogen for several hours to conduct a reaction. The reaction mixture was filtered through Celite. The filtrate was distilled in a vacuum to remove the solvent, giving 9.1 g (corresponding to the quantitative yield) of a crude product as an oil. This oil was used in the subsequent step without further purification.

Mol. formula (M.W.) $C_{12}H_{13}N_3O_2$ (231.26)

$^1$H-NMR δ (CDCl$_3$); 1.40(3H, t, J=7.2 Hz) 4.36(2H, q, J=7.2 Hz) 5.82(2H, br-s) 6.43(1H, dd, J=2.0, 2.4 Hz) 6.75 (1H, d, J=8.8 Hz) 7.61(1H, dd, J=2.4, 8.8 Hz) 7.69(1H, d, J=2.0 Hz) 7.81(1H, d, J=2.4 Hz) 8.12(1H, d, J=2.4 Hz)

Preparative Example 3

6-(Pyrazol-1-yl)quinazoline-2,4-(1H,3H)-dione

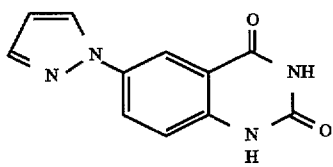

30 g of urea and 5 ml of 1-methyl-2-pyrrolidone were added to 9.1 g (38 mmol) of ethyl 2-amino-5-(pyrazol-1-yl) benzoate. The obtained mixture was stirred at 200° C. for 25 minutes and cooled by allowing to stand, followed by the addition of 150 ml of water under stirring. The crystalline precipitate formed was recovered by filtration, washed with water and air-dried to give about 10 g of a crude crystal. This crude crystal was used in the subsequent step without further purification.

Mol. formula (M.W.) $C_{11}H_8N_4O_2$ (228.21)

$^1$H-NMR δ (DMSO-d$_6$); 6.54(1H, dd, J=1.6, 2.4 Hz) 7.29(1H, d, J=8.8 Hz) 7.75(1H, d, J=1.6 Hz) 8.14(1H, dd, J=2.8, 8.8 Hz) 8.26(1H, d, J=2.4 Hz) 8.55(1H, d, J=2.8 Hz)

Preparative Example 4

2,4-Dichloro-6-(pyrazol-1-yl)quinazoline

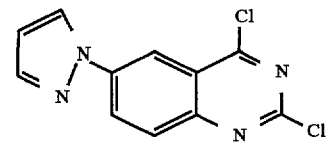

40 ml of phosphorus oxychloride and 10 ml of diisopropylethylamine were added to 3.5 g (13 mmol) of the crude crystal of 6-(pyrazol-1-yl)quinazoline-2,4-(1H, 3H)-dione prepared in the Preparative Example 3. The obtained mixture was heated under reflux for 30 minutes and distilled in a vacuum to remove the solvent. The obtained residue was dissolved in chloroform and the obtained solution was poured onto ice-water. The resulting mixture was filtered to remove unnecessary insolubles. The filtrate was extracted with chloroform. The organic phase was dried over anhydrous magnesium sulfate. The resulting mixture was filtered and the filtrate was distilled in a vacuum to remove the solvent. The obtained residue was purified by column chromatography (with ethyl acetate/hexane) to give 3.25 g of a pale-yellow crystal.

Yield 94%

Mol. formula (M.W.) $C_{11}H_6Cl_2N_4$

M.p. 169°–170° C.

MASS m/e; 265 ($M^+$+1)

Elemental anal. as $C_{11}H_6Cl_2N_4$ calcd. C=49.84 H=2.28 N=21.13 found. C=49.40 H=2.43 N=21.19

$^1$H-NMR δ (DMSO-d$_6$); 6.68(1H, dd, J=1.6, 2.4 Hz) 7.90(1H, d, J=1.6 Hz) 8.20(1H, d, J=9.2 Hz) 8.60(1H, d, J=2.4 Hz) 8.73(1H, dd, J=2.4, 9.2 Hz) 8.87(1H, d, J=2.4 Hz)

Preparative Example 5

5-(Imidazol-1-yl)-2-nitrobenzamide

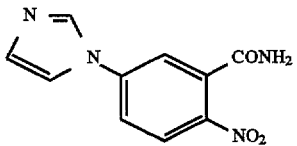

45.5 g (0.668 mol) of imidazole and 61.6 g (0.446 mol) of potassium carbonate were added to a solution of 44.7 g (0.223 mol) of the 5-chloro-2-nitrobenzamide prepared in the Preparative Example 4 in 200 ml of dimethylformamide. The obtained mixture was stirred under heating at 100° C. for 11 hours, followed by the addition of water. The resulting mixture was extracted with ethyl acetate and tetrahydrofuran repeatedly. The obtained organic phases were combined, washed with a saturated aqueous solution of common salt and dried over anhydrous magnesium sulfate. The resulting mixture was filtered to remove the drying agent. The filtrate was distilled in a vacuum to remove the solvent. Ethyl acetate was added to the obtained residue. The obtained mixture was heated and thereafter cooled by allowing to stand, precipitating a crystalline product. This crystalline product was recovered by filtration, washed with ethyl acetate and air-dried to give 27.2 g of a yellow crystal.

Mol. formula (M.W.) $C_{10}H_8N_4O_3$ (232.20)

M.p 206°–207° C.

MASS m/e; 233 ($M^++1$)

Elemental anal. as $C_{10}H_8N_4O_3$ calcd. C=51.73 H=3.47 N=24.13 found. C=51.82 H=3.43 N=24.20

$^1$H-NMR δ (DMSO-$d_6$); 7.18(1H, br-s) 7.85(1H, br-s) 7.97–7.99(3H, m) 8.16–8.19(2H, m) 8.52(1H, br-s)

Preparative Examples 6 and 7

The following compounds were prepared in a similar manner to that of the Preparative Example 5.

Preparative Example 6

2-Nitro-5-(1,2,4-triazol-1-yl)benzamide

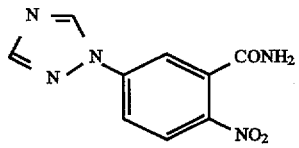

Yield 53%

Mol. formula (M.W.) $C_9H_7N_5O_3$ (233.19)

M.p 211°–212° C.

MASS m/e; 234 ($M^++1$)

Elemental anal. as $C_9H_7N_5O_3$ calcd. C=46.36 H=3.03 N=30.03 found. C=46.10 H=3.06 N=29.59

$^1$H-NMR δ (DMSO-$d_6$); 7.87(1H, br-s) 8.15–8.17(2H, m) 8.24–8.26(2H, m) 8.35(1H, s) 9.54(1H, s)

Preparative Example 7

5-(4-Methylimidazol-1-yl)-2-nitrobenzamide

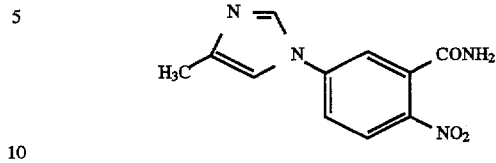

Yield 58%

Mol. formula (M.W.) $C_{11}H_{10}N_4O_3$ (246.23)

M.p 228°–229° C. (dec.)

MASS m/e; 247 ($M^++1$)

Elemental anal. as $C_{11}H_{10}N_4O_3$ calcd. C=53.66 H=4.09 N=22.75 found. C=53.60 H=4.08 N=22.86

$^1$H-NMR δ (DMSO-$d_6$); 2.18(3H, d, J=0.8 Hz) 7.67(1H, m) 7.83(1H, br-s) 7.89–7.92(2H, m) 8.13–8.16(2H, m) 8.40 (1H, d, J=1.6 Hz)

Preparative Example 8

5-(Imidazol-1-yl)-2-nitrobenzonitrile

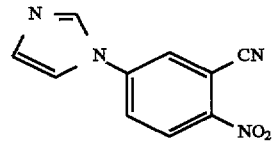

8.0 ml (57 mmol) of trifluoroacetic anhydride was dropped into a solution of 10.0 g (43.1 mmol) of the 5-(imidazol-1-yl)-2-nitrobenzamide prepared in the Preparative Example 5 in 1,4-dioxane (100 ml)/pyridine (10 ml) while stirring the resulting mixture under cooling with ice. The obtained mixture was stirred at room temperature for one hour and poured into water. The resulting mixture was extracted with ethyl acetate.

The organic phase was dried over anhydrous magnesium sulfate. The resulting mixture was filtered and the filtrate was distilled in a vacuum to remove the solvent. The obtained residue was purified by silica gel column chromatography (with acetone/toluene) to give 7.0 g of a yellow crystal.

Yield 76%

Mol. formula (M.W.) $C_{10}H_6N_4O_2$ (214.18)

M.p 179°–180° C.

MASS m/e; 215 ($M^++1$)

Elemental anal. as $C_{10}H_6N_4O_2$ calcd. C=56.08 H=2.82 N=26.16 found. C=56.18 H=2.87 N=26.09

$^1$H-NMR δ (CDCl$_3$); 7.34(1H, m) 7.40(1H, m) 7.83(1H, dd, J=2.4, 8.8 Hz) 7.94(1H, d, J=2.4 Hz) 8.02(1H, m) 8.51(1H, d, J=8.8 Hz)

Preparative Examples 9 and 10

The following compounds were prepared in a similar manner to that of the Preparative Example 8.

Preparative Example 9

2-Nitro-5-(1,2,4-triazol-1-yl)benzonitrile

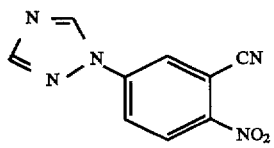

Yield 82%
Mol. formula (M.W.) $C_9H_5N_5O_2$ (215.17)
M.p 153°–154° C.
MASS m/e; 216 (M$^+$+1)
Elemental anal. as $C_9H_5N_5O_2$ calcd. C=50.24 H=2.34 N=32.55 found. C=50.18 H=2.44 N=32.04
$^1$H-NMR δ (DMSO-d$_6$); 8.39(1H, s) 8.43(1H, dd, J=2.4, 9.2 Hz) 8.59(1H, d, J=9.2 Hz) 8.75(1H, d, J=2.4 Hz) 9.6(1H, s)

Preparative Example 10

5-(4-Methylimidazol-1-yl)-2-nitrobenzonitrile

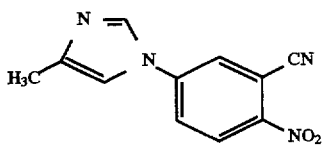

Yield 89%
Mol. formula (M.W.) $C_{11}H_8N_4O_2$ (228.21)
M.p 166°–167° C.
Elemental anal. as $C_{11}H_8N_4O_2$ calcd. C=57.89 H=3.53 N=24.55 found. C=57.84 H=3.49 N=24.59
$^1$H-NMR δ (CDCl$_3$); 2.33(3H, d, J=0.8 Hz) 7.12(1H, m) 7.78(1H, dd, J=2.4, 9.2 Hz) 7.89(1H, d, J=2.4 Hz) 7.94(1H, d, J=1.2 Hz) 8.48(1H, d, J=9.2 Hz)

Preparative Example 11

2-Amino-5-(imidazol-1-yl)benzonitrile

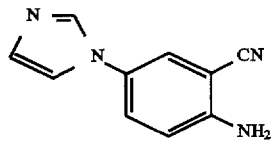

10.0 g (102 mmol) of powdered iron and 20 ml (350 mmol) of acetic acid were added to a solution of 2.00 g (9.34 mmol) of the 5-(imidazol-1-yl)-2-nitrobenzonitrile prepared in the Preparative Example 8 in 60 ml of ethanol. The obtained mixture was heated under reflux for 50 minutes and filtered through Celite. The filtrate was distilled in a vacuum to remove the solvent. The obtained residue was purified by silica gel column chromatography (with methylene chloride/methanol) to give 0.53 g of a yellow crystal.
Yield 31%
Mol. formula (M.W.) $C_{10}H_8N_4$ (184.20)
M.p 186°–187° C. (dec.)
MASS m/e; 185 (M$^+$+1)
$^1$H-NMR δ (DMSO-d$_6$); 6.23(2H, br-s) 6.89(1H, d, J=8.8 Hz) 7.04(1H, t, J=1.2 Hz) 7.57(1H, dd, J=2.4, 8.8 Hz) 7.58(1H, t, J=1.2 Hz) 7.71(1H, d, J=2.4 Hz) 8.06(1H, t, J=1.2 Hz)

Preparative Examples 12 and 13

The following compounds were prepared in a similar manner to that of the Preparative Example 11.

Preparative Example 12

2-Amino-5-(1,2,4-triazol-1-yl)benzonitrile

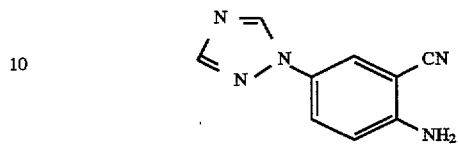

Yield 37%
Mol. formula (M.W.) $C_9H_7N_5$ (185.19)
M.p 201°–202° C.
MASS m/e; 186 (M$^+$+1)
Elemental anal. as $C_9H_7N_5$ calcd. C=58.37 H=3.81 N=37.82 found. C=58.32 H=3.76 N=37.87
$^1$H-NMR δ (DMSO-d$_6$); 6.37(2H, br-s) 6.92(1H, d, J=9.2 Hz) 7.75(1H, dd, J=2.4, 9.2 Hz) 7.88(1H, d, J=2.4 Hz) 8.14(1H, s) 9.07(1H, s)

Preparative Example 13

2-Amino-5-(4-methylimidazol-1-yl)benzonitrile

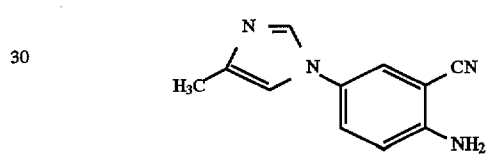

Yield 73%
Mol. formula (M.W.) $C_{11}H_{10}N_4$ (198.23)
Elemental anal. as $C_{11}H_{10}N_4$ calcd. C=66.65 H=5.08 N=28.26 found. C=66.22 H=4.99 N=28.11
$^1$H-NMR 2.28(3H, d, J=0.8 Hz) 4.59(2H, br-s) 6.83(1H, d, J=8.8 Hz) 6.87(1H, m) 7.34(1H, dd, J=2.4, 8.8 Hz) 7.37(1H, d, J=2.4 Hz) 7.61(1H, d, J=1.2 Hz)

Preparative Example 14

2-Ethoxymethyleneamino-5-(imidazol-1-yl)benzonitrile

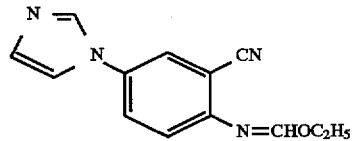

20 ml of ethyl orthoformate and 0.3 ml of trifluoroacetic acid were added to 0.5 g (2.7 mmol) of the 2-amino-5-(imidazol-1-yl)benzonitrile prepared in the Preparative Example 11. The obtained mixture was stirred under heating at 80° C. for one hour and filtered. The obtained filtrate was distilled in a vacuum to remove the solvent. About 0.9 g of a crude product was obtained as a light-brown oil. This crude product was used in the subsequent step without further purification.
Mol. formula (M.W.) $C_{13}H_{12}N_4O$ (240.27)
$^1$H-NMR δ (CDCl$_3$); 1.44(3H, t, J=7.2 Hz) 4.45(2H, q, J=7.2 Hz) 7.15(1H, d, J=8.4 Hz) 7.32(1H, s) 7.35(1H, s) 7.58(1H, dd, J=2.4, 8.4 Hz) 7.67(1H, d, J=2.4 Hz) 7.82(1H, s) 8.23(1H, s)

Preparative Examples 15 and 16

The following compounds were prepared in a similar manner to that of the Preparative Example 14.

Preparative Example 15

2-Ethoxymethyleneamino-5-(1,2,4-triazol-1-yl)benzonitrile

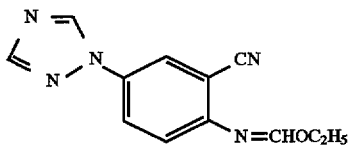

Yellow crystal

Mol. formula (M.W.) $C_{12}H_{11}N_5O$ (241.25)

$^1$H-NMR δ (DMSO-d$_6$); 1.37(3H, t, J=7.2 Hz) 4.35(2H, q, J=7.2 Hz) 7.44(1H, d, J=8.8 Hz) 8.11(1H, dd, J=2.4, 8.8 Hz) 8.20(1H, s) 8.25(1H, s) 8.30(1H, d, J=2.4 Hz) 9.32(1H, s)

Preparative Example 16

2-Ethoxymethyleneamino-5-(4-methylimidazol-1-yl)benzonitrile

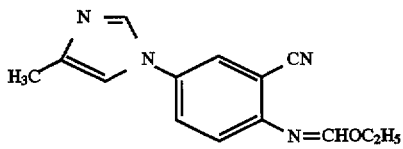

Light-brown crystal

Mol. formula (M.W.) $C_{14}H_{14}N_4O$ (254.29)

$^1$H-NMR δ (DMSO-d$_6$); 1.37(3H, t, J=7.2 Hz) 2.24(3H, d, J=0.8 Hz) 4.35(2H, q, J=7.2 Hz) 7.42(1H, d, J=8.8 Hz) 7.72(1H, s) 7.95(1H, dd, J=2.4, 8.8 Hz) 8.17(1H, d, J=2.4 Hz) 8.19(1H, s) 8.76(1H, s)

Preparative Example 17

3,4-Dihydro-4-imino-3-(3,4-methylenedtoxybenzyl)-6-(imidazol-1-yl)quinazoline

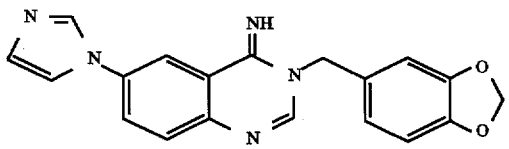

The crude crystal of 2-ethoxymethyleneamino-5-(imidazol-1-yl)benzonitrile Prepared in the Preparative Example 14 was dissolved in 20 ml of methanol, followed by the addition of 0.50 g (3.3 mmol) of piperonylamine. The obtained mixture was stirred at 50° C. for 2 hours, followed by the addition of ether. The resulting mixture was cooled with ice to precipitate a crystalline product. This crystalline product was recovered by filtration, washed with ether and vacuum dried to give 0.29 g of a pale-yellow crystal.

Yield 31%

Mol. formula (M.W.) $C_{19}H_{15}N_5O_2$

M.p 218°–219° C. (dec.)

MASS m/e; 346 (M$^+$+1)

$^1$H-NMR δ (DMSO-d$_6$); 5.11(2H, s) 5.98(2H, s) 6.85(1H, d, J=8.0 Hz) 6.92(1H, d, J=8.0 Hz) 7.04(1H, s) 7.14(1H, s) 7.56(1H, d, J=8.8 Hz) 7.86(1H, s) 7.91(1H, dd, J=2.4, 8.8 Hz) 8.20(1H, s) 8.37(1H, s) 8.48(1H, s) 8.82(1H, s)

Preparative Examples 18 to 20

The following compounds were prepared in a similar manner to that of the Preparative Example 17.

Preparative Example 18

3,4-Dihydro-4-imino-3-(3,4-methylenedioxybenzyl)-6-(1,2,4-triazol-1-yl)quinazoline

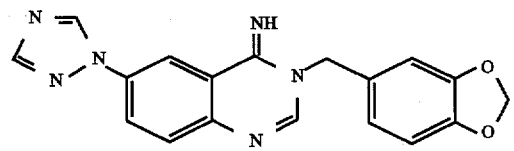

Yield 78%

Mol. formula $C_{18}H_{14}N_6O_2$

M.p 202°–203° C.

MASS m/e; 347 (M$^+$+1)

$^1$H-NMR δ (DMSO-d$_6$); 5.12(2H, s) 5.98(2H, s) 6.85(1H, d, J=8.0 Hz) 6.93(1H, d, J=8.0 Hz) 7.04(1H, s) 7.61(1H, d, J=8.8 Hz) 8.06(1H, dd, J=1.6, 8.8 Hz) 8.23(1H, s) 8.26(1H, s) 8.68(1H, s) 8.80(1H, s) 9.32(1H, s)

Preparative Example 19

3,4-dihydro-4-imino-3-(3,4-methylenedioxybenzyl)-6-(4-methylimidazol-1-yl)quinazoline

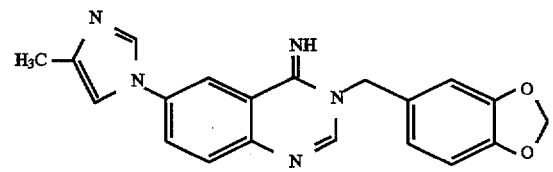

Yield 13%

Mol. formula $C_{20}H_{17}N_5O_2$

M.p 240°–241° C. (dec.)

$^1$H-NMR δ (DMSO-d$_6$); 2.19(3H, s) 5.11(2H, s) 5.98(2H, s) 6.85(1H, d, J=8.4 Hz) 6.92(1H, d, J=8.4 Hz) 7.04(1H, s) 7.54(1H, d, J=8.8 Hz) 7.57(1H, s) 7.86(1H, dd, J=2.4, 8.8 Hz) 8.18(1H, s) 8.25(1H, s) 8.43 (1H, d, J=2.4 Hz) 8.81(1H, s)

Preparative Example 20

3,4-Dihydro-4-imino-3-(3-chloro-4-methoxybenzyl)-6-(4-methylimidazol-1-yl)quinazoline

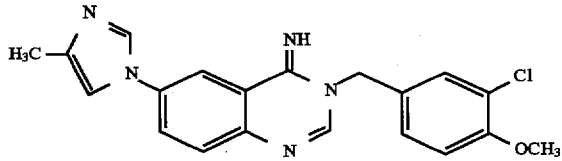

Yield 19%

Mol. formula $C_{20}H_{18}ClN_5O$

M.p 255°–256° C. (dec.)

$^1$H-NMR δ (DMSO-d$_6$); 2.19(3H, d, J=0.8 Hz) 3.82(3H, s) 5.13(2H, s) 7.09(1H, d, J=8.8 Hz) 7.39(1H, br-d)

7.53–7.56(3H, m) 7.86(1H, dd, J=2.4, 8.8 Hz) 8.24(1H, s) 8.25(1H, s) 8.42(1H, s) 8.81(1H, s)

Example 1

2-Chloro-4-(3,4-methylenedioxybenzyl)amino-6-(pyrazol-1-yl)quinazoline

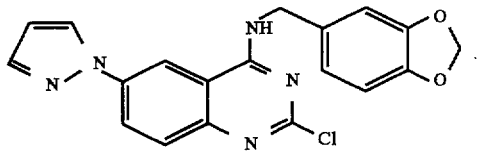

50 ml of tetrahydrofuran, 50 ml of 2-propanol, 15 ml of triethylamine and 1.9 g (13 mmol) of piperonylamine were successively added to 3.2 g (12 mmol) of the 2,4-dichloro-6-(pyrazol-1-yl)quinazoline prepared in the Preparative Example 4. The obtained mixture was heated under reflux for 30 minutes and distilled in a vacuum to remove the solvent. The obtained residue was purified by silica gel column chromatography (with ethyl acetate/hexane) and recrystallization (form ethyl acetate/hexane) to give 3.6 g of a white crystal.

Chem. formula $C_{19}H_{14}ClN_5O_2$

Yield 77%

M.p 209°–10° C.

NMR δ (DMSO-$d_6$); 4.65(2H, d, J=5.6 Hz) 5.96(2H, s) 6.60(1H, dd, J=2.4, 2.0 Hz) 6.85(1H, d, J=8.0 Hz) 6.87(1H, dd, J=8.0, 1.2 Hz) 6.97(1H, d, J=1.2 Hz) 7.73(1H, d, J=8.8 Hz) 7.80(1H, d, J=2.0 Hz) 8.28(1H, dd, J=8.8, 2.4 Hz) 8.50(1H, d, J=2.4 Hz) 8.70(1H, d, J=2.4 Hz) 9.28(1H, t, J=5.6 Hz)

Example 2

2-Chloro-4-(3,4-methylenedioxybenzyl)amino-6-dimethylaminoquinazoline

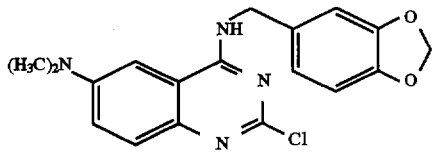

Chem. formula $C_{18}H_{17}ClN_4O_2$

Yield 94%

M.p 226°–7° C. (dec.)

MASS 357 ($M^+$+1)

NMR δ (DMSO-$d_6$); 2.99(6H, s) 4.63(2H, d, J=6.0 Hz) 5.96(2H, s) 6.84(2H, s) 6.93(1H, s) 7.20(1H, d, J=2.8 Hz) 7.37(1H, dd, J=9.2, 2.8 Hz) 7.46(1H, d, J=9.2 Hz) 8.84(1H, t, J=6.0 Hz)

Example 3

2-Chloro-4-(3,4-methylenedioxybenzyl)amino-6-nitroquinazoline

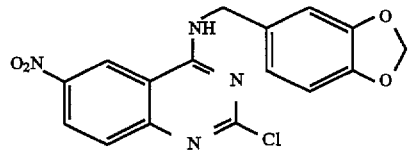

Chem. formula $C_{16}H_{11}ClN_4O_4$

Yield 64%

M.p 237°–8° C.

MASS 359 ($M^+$+1)

NMR δ (DMSO-$d_6$); 4.68(2H, d, J=5.6 Hz) 5.99(2H, s) 6.87–6.91(2H, m) 6.99(1H, s) 7.78(1H, d, J=9.2 Hz) 8.51 (1H, d, J=9.2, 2.4 Hz) 9.42(1H, d, J=2.4 Hz) 9.85(1H, t, J=5.6 Hz)

Example 4

2-Chloro-4-(3,4-methylenedioxybenzyl)amino-6-piperidinoquinazoline

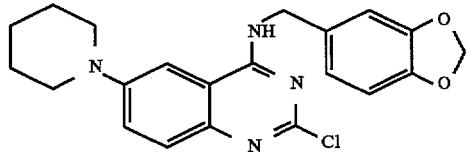

Chem. formula $C_{21}H_{21}ClN_4O_2$

Yield 36%

M.p. 200°–1° C.

MASS 397 ($M^+$+1)

NMR δ (CDCl$_3$); 1.62(2H, m) 1.73(4H, m) 3.21(4H, t, J=5.4 Hz) 4.76(2H, d, J=5.2 Hz) 5.80(1H, t, J=5.2 Hz) 5.97(2H, s) 6.76(1H, d, J=2.4 Hz) 6.81(1H, d, J=8.0 Hz) 6.88(1H, dd, J=8.0, 1.2 Hz) 6.91(1H, d, J=1.2 Hz) 7.48(1H, dd, J=9.2, 2.4 Hz) 7.66(1H, d, J=9.2 Hz)

Example 5

2-Chloro-4-(3,4-methylenedioxybenzyl)amino-6-(2-chloroimidazol-1-yl)quinazoline

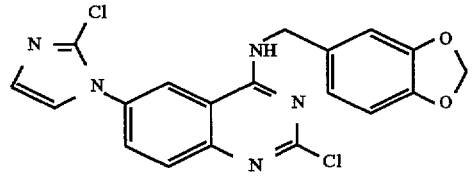

Chem. formula $C_{19}H_{13}Cl_2N_5O_2$

Yield 37%

M.p >280° C.

MASS 414 ($M^+$+1)

NMR δ (DMSO-$d_6$); 4.65(2H, d, J=5.6 Hz) 5.98(2H, s) 6.87(2H, s) 6.98(1H, s) 7.12(1H, d, J=1.6 Hz) 7.64(1H, d, J=1.6 Hz) 7.79(1H, d, J=8.8 Hz) 7.93(1H, dd, J=8.8, 2.4 Hz) 8.51(1H, d, J=2.4 Hz) 9.29(1H, t, J=5.6 Hz)

Example 6

2-(4-Ethoxycarbonylpiperidino)-4-(3,4-methylenedioxybenzyl)amino-6-(pyrazol-1-yl)quinazoline hydrochloride

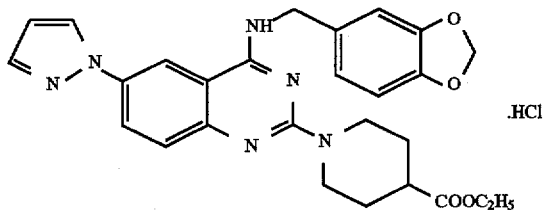

5 ml of tetrahydrofuran, 5 ml of 2-propanol, 2 ml of triethylamine and 1.6 g (9.9 mmol) of ethyl isonipecotate were successively added to 1.5 g (4.0 mmol) of the 2-chloro-4-(3,4-methylenedioxybenzyl)-amino- 6-(pyrazol-1-yl) quinazoline prepared in the Example 1. The obtained mixture was heated under reflux for several hours and distilled in a vacuum to remove the solvent. The obtained residue was purified by silica gel chromatography (with ethyl acetate/ hexane) to give a pale-yellow oil. This oil was crystallized from ethanolic hydrochloric acid/ether. The formed crystal was recovered by filtration, washed with ether and air-dried to give 1.9 g of the title compound as a white crystal.

Chem. formula $C_{27}H_{28}N_6O_4 \cdot HCl$

Yield 91%

M.p 264°–5° C. (decomp.)

MASS 501 ($M^+$+1)

NMR δ (DMSO-$d_6$); 1.21(3H, t, J=7.2 Hz) 1.62(2H, m) 1.98(2H, m) 2.76(1H, m) 3.35(2H, m) 4.10(2H, q, J=7.2 Hz) 4.53(2H, m) 4.71(2H, d, J=5.6 Hz) 5.97(2H, s) 6.62(1H, dd, J=2.4, 1.6 Hz) 6.86(1H, d, J=8.0 Hz) 6.93(1H, dd, J=8.0, 1.6 Hz) 7.04(1H, d, J=1.6 Hz) 7.81(1H, d, J=1.6 Hz) 7.95(1H, d, J=9.2 Hz) 8.31(1H, dd, J=9.2, 2.4 Hz) 8.62(1H, d, J=2.4 Hz) 8.93(1H, d, J=2.4 Hz) 10.40(1H, brs) 12.17(1H, brs)

Example 7

2-(4-Ethoxycarbonylpiperidino)-4-(3,4-methylenedioxybenzyl)amino-6-dimethylaminoquinazoline

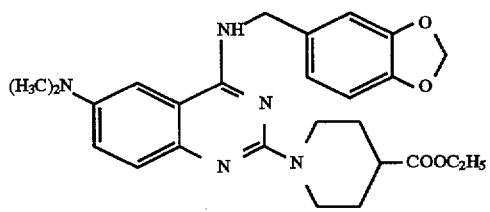

The title compound was prepared from the 2-chloro-4-(3, 4-methylenedioxybenzyl)amino-6-dimethylaminoquinazoline prepared in the Example 2.

Chem. formula $C_{26}H_{31}N_5O_4$

Yield 89%

M.p 168°–9° C.

NMR δ (CDCl$_3$); 1.26(3H, t, J=7.2 Hz) 1.73(2H, m) 1.96(2H, m) 2.52(1H, m) 2.95(6H, s) 2.99(2H, m) 4.14(2H, q, J=7.2 Hz) 4.72(2H, d, J=5.2 Hz) 4.76(2H, m) 5.55(1H, brs) 5.95(2H, s) 6.51(1H, brd, J=2.4 Hz) 6.79(1H, d, J=7.6 Hz) 6.87(1H, dd, J=7.6, 1.6 Hz) 6.92(1H, d, J=1.6 Hz) 7.23(1H, brdd, J=9.2, 2.4 Hz) 7.44(1H, brd, J=9.2 Hz)

Example 8

2-(4-Ethoxycarbonylpiperidino)-4-( 3,4-methylenedioxybenzyl)amino-6-dimethylnitroquinazoline

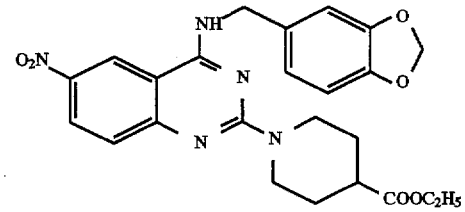

The title compound was prepared from the 2-chloro-4-(3, 4-methylenedioxybenzyl)amino-6-nitroquinazoline prepared in the Example 3.

Chem. formula $C_{24}H_{25}N_5O_6$

Yield 86%

M.p 229°–30° C.

NMR δ (CDCl$_3$); 1.27(3H, t, J=7.2 Hz) 1.73(2H, m) 2.00(2H, m) 2.60(1H, m) 3.14(2H, m) 4.16(2H, q, J=7.2 Hz) 4.69(2H, d, J=5.6 Hz) 4.85(2H, m) 5.97(2H, s) 6.00(1H, brs) 6.81(1H, d, J=8.0 Hz) 6.86(1H, dd, J=8.0, 1.6 Hz) 6.89(1H, d, J=1.6 Hz) 7.38(1H, d, J=9.2 Hz) 8.27(1H, dd, J=9.2, 2.4 Hz) 8.47(1H, d, J=2.4 Hz)

Example 9

2-(4-Carboxypiperidino)-4-(3,4-methylenedioxybenzyl)amino-6-(pyrazol-1-yl)quinazoline

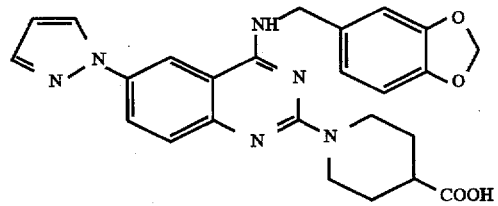

The title compound was prepared from the 2-(4-ethoxycarbonylpiperidino)-4-(3,4-methylenedioxybenzyl)amino-6-(pyrazol-1-yl)quinazoline hydrochloride prepared in the Example 6.

Chem. formula $C_{25}H_{24}N_6O_4$

Yield 99%

M.p 222°–3° C. (decomp.)

NMR δ (DMSO-$d_6$);

1.47(2H, m) 1.86(2H, m) 2.52(1H, m) 3.05(2H, m) 4.60 (2H, m) 4.63(2H, d, J=5.2 Hz) 5.96(2H, s) 6.56(1H, dd, J=2.4, 1.6 Hz) 6.84(1H, d, J=8.0 Hz) 6.89(1H, dd, J=8.0, 1.2 Hz) 6.98(1H, d, J=1.2 Hz) 7.44(1H, br) 7.75(1H, d, J=1.6 Hz) 8.04(1H, br) 8.41(1H, d, J=2.4 Hz) 8.50(1H, brs) 12.20(1H, brs)

Example 10

2-(4-Carboxypiperidino)-4-(3,4-methylenedioxybenzyl)amino-6-dimethylaminoquinazoline

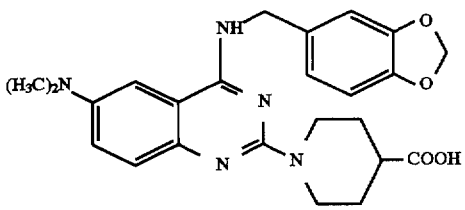

The title compound was prepared from the 2-(4-ethoxycarbonylpiperidino)-4-(3,4-methylenedioxybenzyl)amino-6-dimethylaminoquinazoline prepared in the Example 7.

Chem. formula $C_{24}H_{27}N_5O_4$

Yield quant.

M.p 269°–70° C. (dec.)

NMR δ (DMSO-$d_6$); 1.42(2H, m) 1.80(2H, m) 2.44(1H, m) 2.92(2H, m) 2.92(6H, s) 4.55(2H, m) 4.60(2H, d, J=6.0 Hz) 5.95(2H, s) 6.82(1H, d, J=8.0 Hz) 6.86(1H, dd, J=8.0, 1.2 Hz) 6.94(1H, d, J=1.2 Hz) 7.16(1H, brs) 7.22(2H, brs) 8.38(1H, brs) 2.10(1H, brs)

Example 11

2-(4-Carboxypiperidino)-4-(3,4-methylenedioxybenzyl)amino-6-nitroquinazoline

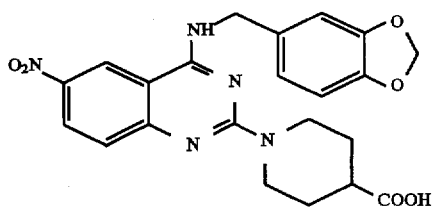

The title compound was prepared from the 2-(4-ethoxycarbonylpiperidino)-4-(3,4-methylenedioxybenzyl)amino-6-nitroquinazoline prepared in the Example 8.

Chem. formula $C_{22}H_{21}N_5O_6$

Yield 74%

M.p 261°–2° C. (dec.)

NMR δ (DMSO-$d_6$); 1.45(2H, m) 1.87(2H, m) 2.54(1H, m) 3.09(2H, m) 4.59(2H, d, J=5.2 Hz) 4.67(2H, m) 5.96(2H, s), 6.83(1H, d, J=8.0 Hz) 6.88 (1H, dd, J=8.0, 1.6 Hz) 6.96(1H, d, J=1.6 Hz) 7.27(1H, d, J=9.2 Hz) 8.21(1H, dd, J=9.2, 2.4 Hz) 9.12(1H, d, J=2.4 Hz) 9.13(1H, brt) 12.22 (1H, brs)

Example 12

2-(4-Ethoxycarbonylpiperidino)-4-(3,4-methylenedioxybenzyl)amino-6-aminoquinazoline dihydrochloride

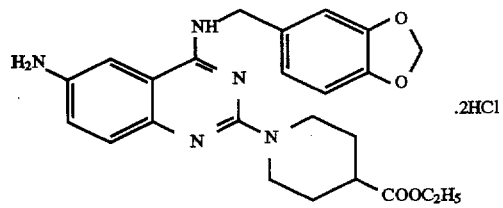

The title compound was prepared from the 2-(4-carboxypiperidino)-4-(3,4-methylenedioxybenzyl)amino-6-nitroquinazoline prepared in the Example 11.

Chem. formula $C_{24}H_{27}N_5O_6\cdot 2HCl$

Yield 89%

M.p 236°–7° C. (dec.)

NMR δ (DMSO-$d_6$); 1.20(3H, t, J=7.2 Hz) 1.58(2H, m) 1.95(2H, m) 2.74(1H, m) 3.31(2H, m) 4.09(2H, q, J=7.2 Hz) 4.53(2H, m) 4.67(2H, d, J=5.6 Hz) 5.97(2H, s) 6.84(1H, d, J=8.0 Hz) 6.89(1H, dd, J=8.0, 1.6 Hz) 6.99(1H, d, J=1.6 Hz) 7.59(1H, brd, J=8.8 Hz) 7.91(1H, d, J=8.8 Hz) 7.95(1H, brs) 10.21(1H, brs) 12.26(1H, brs)

Example 13

2-(4-Carboxypiperidino)-4-(3,4-methylenedioxybenzyl)amino-6-(tetrazol-1-yl)quinazoline hydrochlorine

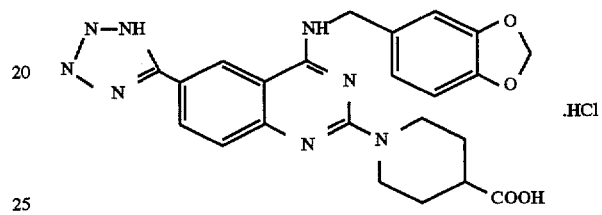

Chem. formula $C_{23}H_{22}N_8O_4\cdot HCl$

Yield 88%

M.P. >270° C.

NMR δ (DMSO-$d_6$); 1.62(2H, m) 1.98(2H, m) 2.68(1H, m) 3.44(2H, m) 4.55(2H, m) 4.71(2H, d, J=5.6 Hz) 5.98(2H, s) 6.87(1H, d, J=8.0, Hz) 6.92(1H, dd, J=8.0, 1.6 Hz) 7.02(1H, d, J=1.6 Hz) 8.05(1H, d, J=8.8 Hz) 8.39(1H, dd, J=8.8, 1.6 Hz) 9.12(1H, d, J=1.6 Hz) 10.29(1H, brt, J=5.6 Hz)

Example 14

4-(3,4-Methylenedioxybenzyl)amino-6-(imidazol-1-yl)quinazoline

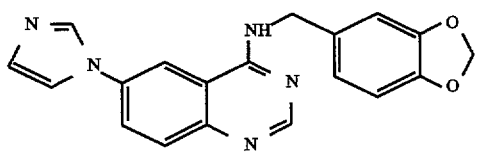

Chem. formula $C_{19}H_{15}N_5O_2$

Yield 54%

M.p. 209°–210° C. (dec.)

MASS 346 (M$^+$+1)

NMR δ (DMSO-$d_6$); 4.73(2H, d, J=5.6 Hz) 5.97(2H, s) 6.85(1H, d, J=8.0 Hz) 6.89(1H, dd, J=8.0, 1.6 Hz) 6.97(1H, d, J=1.6 Hz) 7.17(1H, s) 7.82(1H, s) 7.83(1H, d, J=8.8 Hz) 8.10(1H, dd, J=8.8, 2.4 Hz) 8.34(1H, s) 8.49(1H, s) 8.55(1H, d, J=2.4 Hz) 8.74(1H, t, J=5.6 Hz)

Example 15

4-(3,4-Methylenedioxybenzyl)amino-6-(1,2,4-triazol-1-yl)quinazoline

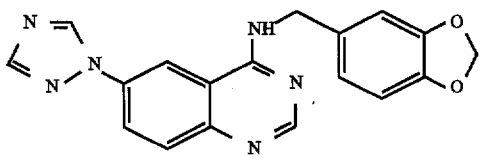

Chem. formula C₁₈H₁₄N₆O₂  
Yield 93%  
M.p 247°–8° C. (decomp.)  
MASS 347 (M⁺+1)  
NMR δ (DMSO-d₆); 4.71(2H, d, J=5.6 Hz) 5.97(2H, s) 6.85(1H, d, J=8.0 Hz) 6.89(1H, dd, J=8.0, 1.6 Hz) 6.97(1H, d, J=1.6 Hz) 7.87(1H, d, J=9.2 Hz) 8.26(1H, dd, J=9.2, 2.4 Hz) 8.31(1H, s) 8.51(1H, s) 8.78(1H, d, J=2.4 Hz) 8.91(1H, t, J=5.6 Hz) 9.29(1H, s)

Example 16

4-(3,4-Methylenedioxybenzyl)amino-6-(4-methylimidazol-1-yl)quinazoline

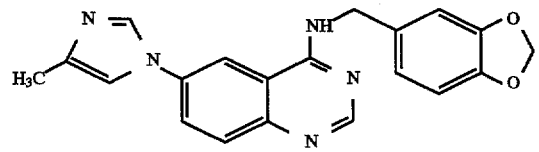

Chem. formula C₂₀H₁₇N₅O₂  
Yield 55%  
M.p 179°–80° C.  
NMR δ (CDCl₃); 2.27(3H, d, J=0.8 Hz) 4.81(2H, d, J=5.2 Hz) 5.95(2H, s) 6.74(1H, brt) 6.79(1H, d, J=7.6 Hz) 6.89 (1H, dd, J=7.6, 1.6 Hz) 6.92(1H, d, J=1.6 Hz) 7.05(1H, m) 7.73(1H, dd, J=8.8, 2.4 Hz) 7.77(1H, d, J=1.6 Hz) 7.78(1H, d, J=2.4 Hz) 7.95(1H, d, J=8.8 Hz) 8.72(1H, s)

Example 17

4-(3-Chloro-4-methoxybenzyl)amino-6-(4-methylimidazol-1-yl)quinazoline

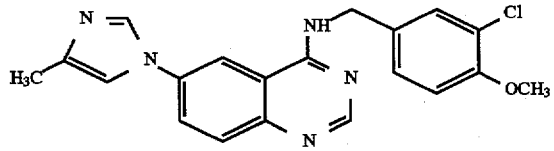

Chem. formula C₂₀H₁₈ClN₅O

Yield 48%

M.p 135°–6° C.

NMR δ (CDCl₃); 2.24(3H, s) 3.87(3H, s) 4.84(2H, d, J=5.2 Hz) 6.88(1H, d, J=8.4 Hz) 7.04(1H, s) 7.26(1H, brt) 7.30(1H, dd, J=8.4, 2.4 Hz) 7.44(1H, d, J=2.4 Hz) 7.72(1H, dd, J=9.2, 2.0 Hz) 7.73(1H, s) 7.89(1H, d, J=2.0 Hz) 7.94(1H, d, J=9.2 Hz) 8.71(1H, s)

We claim:

1. A quinazoline derivative represented by the following formula (I) or a pharmacologically acceptable salt thereof:

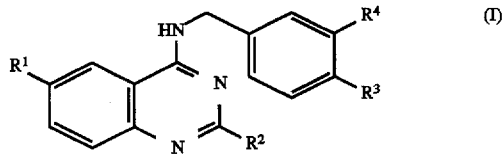

wherein R¹ is selected from pyrazolyl, imidazolyl, substituted imidazolyl, triazolyl, tetrazolyl, piperidyl, a nitro group or a —NR⁵R⁶ group wherein R⁵ and R⁶ may be the same or different from each other and each represent a hydrogen atom or a lower alkyl group;

R² is a hydrogen atom with the proviso when R¹ is an amino group, then R² is not a hydrogen atom, a halogen atom or a group represented by the following formula

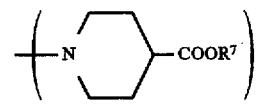

wherein R7 is a hydrogen atom or a lower alkyl group;

R³ and R⁴ each represent a halogen atom or a lower alkoxy group, or together form a methylenedioxy group or ethylenedioxy group.

2. A composition comprising a compound of claim 1 together with a carrier or diluent.

3. A method for treating ischemic heart disease, angina pectoris, hypertension, heart failure or asthma, which comprises administering a mammal with a pharmacologically effective amount of the compound as claimed in claim 1, or a pharmacologically acceptable salt thereof.

4. The method as claimed in claim 3, in which the subject is a human being.

* * * * *